(12) United States Patent
Lademann et al.

(10) Patent No.: US 9,345,629 B2
(45) Date of Patent: May 24, 2016

(54) METHOD FOR DECONTAMINATING THE SKIN WITH TEXTILE COMPOSITE MATERIAL

(71) Applicant: SNS Nano Fiber Technology, LLC, Hudson, OH (US)

(72) Inventors: Jurgen Lademann, Berlin (DE); Laura M. Frazier, Stow, OH (US); Woraphon Kataphinan, Akron, OH (US)

(73) Assignee: SNS NANO FIBER TECHNOLOGY, LLC, Hudson, OH (US)

( * ) Notice: Subject to any disclaimer, the term of this patent is extended or adjusted under 35 U.S.C. 154(b) by 439 days.

(21) Appl. No.: 14/075,586

(22) Filed: Nov. 8, 2013

(65) Prior Publication Data
US 2014/0093548 A1    Apr. 3, 2014

Related U.S. Application Data

(62) Division of application No. 12/850,138, filed on Aug. 4, 2010.

(60) Provisional application No. 61/236,633, filed on Aug. 25, 2009.

(51) Int. Cl.
| | |
|---|---|
| *A61B 17/50* | (2006.01) |
| *A61F 13/53* | (2006.01) |
| *A61F 13/02* | (2006.01) |
| *A61L 15/56* | (2006.01) |
| *A61L 15/58* | (2006.01) |
| *A61F 13/00* | (2006.01) |

(52) U.S. Cl.
CPC ............. *A61F 13/53* (2013.01); *A61F 13/0203* (2013.01); *A61L 15/56* (2013.01); *A61L 15/58* (2013.01); *A61F 2013/00187* (2013.01); *A61F 2013/00234* (2013.01); *A61F 2013/00425* (2013.01); *A61F 2013/00536* (2013.01); *A61F 2013/00753* (2013.01)

(58) Field of Classification Search
CPC ................ A61F 13/0203; A61F 13/53; A61F 2013/00187; A61F 2013/00234; A61F 2013/00425; A61F 2013/00536; A61F 2013/00753; A61L 15/56; A61L 15/58
USPC ....................... 606/131; 424/402, 449; 602/52
See application file for complete search history.

(56) References Cited

U.S. PATENT DOCUMENTS

| | | | | |
|---|---|---|---|---|
| 2006/0246798 | A1* | 11/2006 | Reneker | A61F 13/531 442/59 |
| 2008/0255531 | A1* | 10/2008 | Ring | A61L 15/60 604/368 |
| 2010/0121297 | A1* | 5/2010 | Salim | A61F 13/0203 604/375 |

* cited by examiner

*Primary Examiner* — Katherine M Shi
(74) *Attorney, Agent, or Firm* — Weisun Rao; Greenberg Traurig, LLP

(57) ABSTRACT

The present invention provides a method of decontaminating human skin from noxious substances without a washing and/or massage procedure, wherein the method comprises applying a textile composite to a contaminated skin area for a predetermined period of time, wherein a washing procedure or a massage procedure is not utilized; and removing the textile composite from the contaminated skin area.

6 Claims, 8 Drawing Sheets

METHOD FOR DECONTAMINATING THE SKIN WITH TEXTILE COMPOSITE MATERIAL

CROSS-REFERENCE TO RELATED APPLICATIONS

This is a divisional application of and claiming priority from U.S. application Ser. No. 12/850,138, filed on Aug. 4, 2010, which in turn claims priority from U.S. Provisional Application No. 61/236,633, filed on Aug. 25, 2009.

BACKGROUND OF THE INVENTION

Previously, a decontamination of the skin after contact with hazardous substances released by chemical and reactor accidents, for example, is carried out mainly by intensive washing using different detergents and solvents. However, this way of proceeding has the disadvantage that it is hardly possible or not possible at all to extract particles of noxious substances which have already penetrated the hair follicles or the upper skin cell layer, i.e. the upper corneocytes of the stratum corneum, which constitute a long-term reservoir for topically applied substances. Furthermore, in case of a decontamination, the noxious substances which are to be removed from the skin surface are partially rubbed in the hair follicles and the skin furrows by an intensive washing. In this way, the long-term effect of the noxious substances in the skin may even be increased. Additionally, efficient methods for skin decontamination may be not only important in the case of industrial or research accidents, but also in relation to terrorist attacks. Accordingly, there is a need to provide a material and method for decontaminating the skin which permits an effective removal of noxious substances from the skin surface without washing.

DE-A 102005054698 discloses a nanofiber nonwoven finished with a superabsorbent, the nanofiber nonwoven being used for the absorption and/or the slow release of different fluids, in particular of body liquids.

Nonwovens made of textile fibers having a diameter of less than 10 µm, preferably of less than 1 µm, are defined as "nanofiber nonwovens". Nanofiber nonwovens are known for example from U.S. Pat. No. 4,043,331 and from International Patent Application WO 01/27365. These documents also disclose methods for the manufacturing of these nonwovens, and are incorporated herein by reference.

The term "superabsorbent" denotes polymer materials which can absorb water or other fluids up to a thousand times their mass, whereby swelling to form a gel. Superabsorbents and methods of their manufacture are generally known from *Ullmanns Encyclopedia of Industrial Chemistry*, 6th Ed., Vol. 35, pp. 73 ff., 2003. DE-A 102005054698 describes superficially post-cured superabsorbents which have a more strongly post-cured shell and a less strongly postcured core which serves to absorb fluids. Compared to superabsorbents that are not post-cured, superabsorbents having such a structure show a smaller "gel blocking" effect. This effect is caused by a clogging of swollen superabsorbent particles or superabsorbent particles which have started to swell, and has a negative impact on the absorbency and the retention ability of the superabsorbent.

Accordingly, the use of a nanofiber nonwoven in a textile composite material, wherein the nanofiber nonwoven is filled with a superabsorbent, would allow for the decontaminating of the skin from noxious substances without washing.

BRIEF SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

The subject matter disclosed and claimed herein, in one aspect thereof, comprises the use of a nanofiber nonwoven in a textile composite material for decontaminating of skin from noxious substances without a washing procedure, wherein the nanofiber nonwoven is filled with a superabsorbent for absorbing and retaining the noxious substances from the skin.

In a preferred embodiment, the textile composite material comprises an active layer comprised of the nanofiber nonwoven and the superabsorbent. Preferably, the active layer is comprised of at least one cover layer which is formed from a nanofiber nonwoven without a superabsorbent, and a base layer comprising the nanofiber nonwoven filled with the superabsorbent.

In another embodiment, the active layer has a sandwich structure comprising a top and bottom cover layer formed from a nanofiber nonwoven without a superabsorbent, and a base layer comprising the nanofiber nonwoven filled with the superabsorbent, the base layer being arranged between said top and bottom cover layer. The cover layers help to prevent the superabsorbent from bleeding out of the base layer, and provide a softer feel to the textile composite material.

In order to form the active layer, the superabsorbent may be dusted on the nanofiber nonwoven and mechanically held in the nanofiber structure. Alternatively, the superabsorbent can be applied to the nanofibers during the spinning process, or can be added to the polymer solution before spinning.

In a further aspect of the invention, the nanofiber nonwoven may be used in the manufacture of the textile composite material for decontaminating of skin wherein the composite material further comprises a flexible carrier layer connected to the active layer.

In another embodiment, a textile composite material for decontaminating of skin comprises a flexible carrier layer and an active layer connected to said carrier layer, wherein the active layer comprises a nanofiber nonwoven filled with a superabsorbent for absorbing and retaining noxious substances from the skin.

Within the context of a decontamination of the skin, the textile composite material is applied to the skin areas contaminated by particles of noxious substances such that the active layer comes in contact with the concerned parts of the skin. The carrier layer may be used for the shaping and, owing to its flexibility, for the optimum shape adaptation of the composite material to the skin surface.

The nanofiber nonwoven contained in the active layer and finished with a superabsorbent is particularly absorbent due to the high capillarity in the nonwoven, and absorbs the noxious substances, that have to be removed, according to the existing concentration gradient between the skin surface and the nonwoven material. The noxious substances can then be effectively stored and retained by the superabsorbent. After an appropriate decontamination time of preferably about 30 seconds to 30 minutes, more preferably about 1 to 5 minutes, depending on the nature of the noxious substance, the textile composite material including the absorbed noxious substances can be removed again from the skin.

Since this type of decontamination of the skin is solely based on the absorbing effect of the nanofiber nonwoven finished with a superabsorbent, a rubbing of the noxious substances into the hair follicles and the skin furrows is avoided, and the noxious substance particles are thus prevented from further entering the hair follicles or the upper cell layer of the corneocytes. The risk of a long-term effect of the noxious substances in the skin is therefore reliably excluded.

According to a preferred embodiment of the invention, at least one of the carrier layer and the active layer are designed to stimulate the production of sweat by the skin. An increased production of sweat by the parts of the skin covered by the active layer or carrier layer increases the decontaminating effect of the textile composite material. The sweat flushes out the noxious substances having already penetrated the hair follicles and the upper cell layer of the corneocytes. The sweat, along with these noxious substances and the particles of noxious substances still present on the skin surface, is then absorbed by the superabsorbent in the nanofiber nonwoven and retained therein.

In a specific embodiment, the textile composite material has a carrier layer that is impermeable to water vapor. The carrier layer which is impermeable to water vapor closes the active layer lying on the contaminated skin surface in a damp-tight manner and thus stimulates the production of sweat in the enclosed skin area. The skin surface cannot release the sweat produced there to the environment by evaporation. Rather, the sweat, along with the noxious substances flushed out, is absorbed by the nanofiber nonwoven and retained in the superabsorbent.

According to a further embodiment, at least one of the active layer and the carrier layer are configured to be permeable to heat radiation. The skin areas concerned which are covered by the textile composite material can then be purposefully heated using heat radiators, for example, or a chemical reaction producing heat. A quick and controlled stimulation of the production of sweat in the contaminated skin area is thereby obtained. The heat transfer between the active layer and the skin surface may take place by heat conduction. It is preferable that both the carrier layer and the active layer are permeable to heat radiation.

According to another embodiment, the carrier layer and/or the active layer of the textile composite material is configured so as to be heat conducting. It is, for example, possible to insert metallic fibers or metallic filaments into the carrier layer and/or the active layer, or provide the active layer with a metallic coating. As in the embodiment described above, the skin areas concerned can be purposefully heated using appropriate heating sources such as, e.g., an electrical heating element, and the production of sweat can therefore be stimulated.

In still another embodiment, the active layer may contain an agent promoting the production of sweat, for example by applying a sweat promoting agent onto the surface of the active layer that faces the skin. The textile composite material then acts like a transdermal system, the agent being absorbed by the skin first and stimulating the production of sweat. In contrast to transdermal systems, the sweat promoting agent does not require a long-term effect since the production of sweat is to be locally restricted and is intended to occur only for the duration of the decontamination. The sweat produced in the contaminated skin area, along with the noxious substances, flushed out and the excessive agent, is then absorbed by the nanofiber nonwoven and retained in the superabsorbent.

The embodiments described above can be combined with each other in any way. The carrier layer can be at the same time impermeable to water vapor and heat conducting or permeable to heat radiation, and/or the active layer can contain an agent promoting the production of sweat. Further combinations are also conceivable and considered to be within the scope of the invention.

The carrier layer and the active layer can be formed integrally with each other. For example, the carrier layer can be a woven fabric, and the nanofibers of the active layer can be firmly spun onto and with the woven fabric filaments of the carrier layer. Preferably, the carrier layer and the active layer are bonded to each other. The layers can then be produced separately, so as to have the respective desired properties, and then bonded to each other by chemical, thermal or physical bonding as is generally known in the art.

According to a preferred embodiment, the carrier layer is elastic, allowing for optimum adaptation of the textile composite material to the skin. If the carrier layer is elastic, then the textile composite material can be adapted to the shape of the skin surface by contraction and/or expansion.

In another embodiment, the carrier layer is configured so as not to be expandable. During the absorption of noxious substances flushed out by the sweat, the superabsorbent contained in the active layer swells as a result of which the volume of the active layer increases. Since the carrier layer which is arranged on the side of the active layer that faces away from the skin, cannot expand, this increase in volume results in that the contact between the active layer and the skin surface is intensified and the active layer rests more firmly on the skin area concerned, and thus further increases the effectiveness of the decontamination.

According to a further embodiment, an adhesive layer is provided on the surface of the composite material that faces the skin to fasten the textile composite material to the skin. In this embodiment, the carrier layer preferably has a planar surface area which is larger than a planar surface area of the active layer so that the carrier layer overlaps the active layer thereby encircling the rim of the active layer. The overlapping edge part of the carrier layer is provided with the adhesive layer for connecting the composite material with the skin.

In addition, the surface of the active layer that faces away from the carrier layer, i.e. the skin-side surface, can be provided with an adhesive layer. This leads to an even better contact of the active layer with the skin which in turn leads to an improvement of the decontaminating effect.

Furthermore, the adhesive layer applied to the active layer can be designed to remove the upper cell layer of the corneocytes from the skin. When removing the textile composite system from the skin area to be decontaminated, the upper cell layer of the corneocytes, along with the noxious substance particles having already entered the latter, is thus extracted in a non-invasive way, and the proportion of the removed noxious substances is thus again increased.

According to a specific embodiment, the composite textile material comprises the flexible carrier layer, and a first and second active layer, wherein the first active layer is provided with a metal coating. The nanofiber nonwoven constituting the first active layer is produced to form peaks and valleys. The valleys of the first active layer are filled with the second active layer. At least the second active layer is composed of the nanofiber nonwoven filled with superabsorbent. Preferably, both of the first and second active layer include the superabsorbent. The adhesive layer is provided on the metallic coating, or on the rim portion of the carrier layer, as described above.

The active layer may also comprise a color indicator to indicate the production of sweat. Owing to this addition, the optimum time to remove the material from the skin can be indicated to the user of the textile composite material. The colors of the color indicator change if the nanofiber nonwoven has absorbed an amount of sweat that is sufficient for decontaminating and/or the capacity of the superabsorbent to absorb liquid has been exhausted. The color indicator may be combined with the superabsorbent and incorporated into the active layer, for example by adding the combined superabsorbent and color indicator to the polymer melt or solution before spinning of the nanofiber nonwoven.

Preferably, the textile composite material can be configured as a cloth, a compress, a dressing or a plaster, also as an article of clothing or part of clothing for application on larger surfaces.

In a preferred embodiment, the polymer particles of the superabsorbent are a screening fraction having a particle size distribution of d50=55-100 μm and d100=100-150 μm, and are not crushed after the superficial postcure of the shell, prior to the incorporation of the superabsorbent into the nanofiber nonwoven.

The nanofiber nonwovens can be produced through melt spinning, electrospinning, or gas jet spinning (NGJ) of suitable polymers. It is also contemplated that part of the nanofibers in the nonwoven can be replaced by microfibers.

The superabsorbent may be dusted onto a sheet of the nanofiber nonwoven and mechanically integrated into the nanofiber structure. This process can be repeated until the desired filling level of superabsorbent is achieved. Alternatively, the superabsorbent can be applied to the nanofibers during the spinning process when the fiber dries and solidifies. Most preferably, the superabsorbent is homogeneously dispersed in a polymer solution which is then subjected to spinning into a nanofiber nonwoven including the superabsorbent embedded in the fiber structure.

In view of the intended use of the textile composite material for decontaminating the skin, the nanofiber nonwoven preferably has at least one or more of the following physical properties:

a) A fiber diameter of between 0.001 μm and 10 μm, preferably between 0.1 μm and 1.5 μm, and most preferably between 300 nm and 900 nm;
b) An average pore size of between 0.01 μm to 500 μm, preferably less than 250 μm, more preferably less than 100 μm;
c) A porosity, that is a percentage of the total volume of the nonwoven which is free space, of between 40% and 90%, preferably between 70% and 90%;
d) A thickness of the active layer of between 0.1 mm to 2 mm;
e) A density of between 0.8 to 1.5 g/cm3;
f) A mass per unit area of between 50 to 500 g/m2, preferably between 50 and 400 g/m2, more preferably of between 150 to 250 g/m2;
g) A breaking force and elongation (strip method), according to EDANA standard WSP 110.4 (05), of 1.5-2 MPa and 485 to 500%;
h) An absorbency (tb) in saline (0.9% NaCl in water, 30 min), as measured in the teabag test in accordance with EDANA standard test WSP 240.2 (05), of between about 8 g/g and 10 g/g;
i) A retention capacity (CRC) for saline (0.9% NaCl in water, 30 min), as measured in accordance with EDANA standard test WSP 241.2 (05), of between about 6 g/g to 8 g/g.

Further, the active layer composed of the nanofiber nonwoven filled with the superabsorbent preferably has at least one or more of the following properties:

j) A filling level of superabsorbent (SAP), that is calculated as weight by weight of dry material, of between about 10 and 80%, preferably between about 40 and 80%, and most preferably between about 50 to 70%;
k) An absorbency (tb) in saline (0.9% NaCl in water, 30 min), as measured in the teabag test in accordance with EDANA standard test WSP 240.2 (05) of between 20 g/g and 50 g/g, preferably between 25 g/g and 31 g/g, at an SAP filling level of 50%, and between about 38 g/g and 45 g/g at an SAP filling level of 75%;
l) A retention capacity (CRC) for saline (0.9% NaCl in water, 30 min), as measured in the centrifuge test according to EDANA standard test WSP 241.2 (05), of between 14 g/g and 40 g/g, preferably between 20 g/g and 35 g/g for SAP filling levels of between 50% and 75%; and
m) A contact angle as measured at 22° C. and 55% relative humidity (Fibro DAT™ of Rycobel, Belgium) of between 110° and 125°.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and is intended to include all such aspects and their equivalents. Other advantages and novel features will become apparent from the following detailed description when considered in conjunction with the drawings.

DETAILED DESCRIPTION OF THE INVENTION

Figure 1:
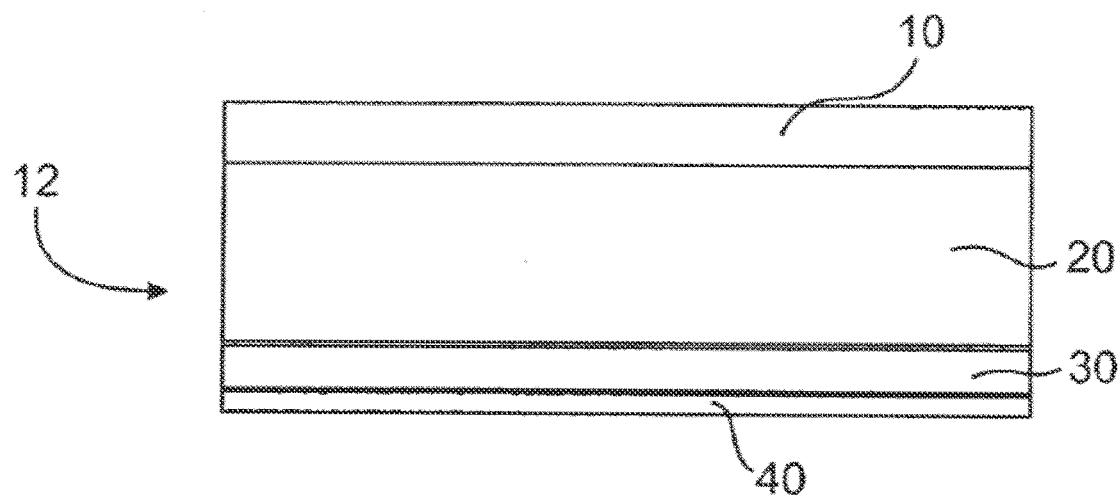
FIG. 1 illustrates a schematic cross-sectional view of the textile composite material in accordance with principles of the present invention.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof.

Typically, a decontamination of the skin after contact with noxious substances by intensive washing using different detergents and solvents, does not extract particles of noxious substances which have already penetrated the hair follicles or the upper skin cell layer, i.e. the upper corneocytes of the stratum corneum, which constitute a long-term reservoir for topically applied substances. Usually, hair follicles act as a long term reservoir for topically applied substances providing significantly increased storage times in comparison to the stratum corneum. Additionally, the hair follicles contain or are surrounded by several important target structures, such as blood capillaries, stem and dendritic cells. Here, hazardous substances can exhibit strong destructive activities. Furthermore, in case of a decontamination, the noxious substances which are to be removed from the skin surface are partially rubbed in the hair follicles and the skin furrows by an intensive washing. In this way, the long-term effect of the noxious substances in the skin may even be increased. Thus, a material for decontaminating the skin which permits an effective removal of noxious substances from the skin surface must not utilize washing.

Accordingly, the absorbent textile composite material disclosed does not utilize washing to decontaminate the skin. The textile composite material comprises a carrier layer and an active layer connected to the carrier layer. The active layer comprises a nanofiber nonwoven filled with a superabsorbent to absorb and retain noxious substances from the skin. The advantage of decontamination with the absorbent textile composite materials is that it can be carried out immediately without the utilization of water, which is not always available at the required time. Efficient methods for skin decontamination may be not only important in the case of industrial or research accidents, but also in relation to terrorist attacks.

Referring initially to the drawings, FIG. 1 illustrates an absorbent textile composite material 12. The absorbent textile composite material 12 comprises a carrier layer 10, an active layer 20, an adhesive layer 30 and a protective layer 40. The carrier layer 10 may be a film or a textile web, and is preferably made of polymers selected from the group comprising polypropylene, polyurethane, polycaprolactone, nylon, polyimide, polyvinyl alcohol, polyvinylamine, polyester including polyethylene terephthalate, polyacrylonitrile, polyethylene oxide and copolymers thereof. More preferably, the carrier layer 10 is hydrophobic and made of a material impermeable to water vapor, preferably polyethylene terephthalate (PET) or polypropylene. The carrier layer 10 which is impermeable to water vapor closes the active layer 20 lying on the contaminated skin surface in a damp-tight manner and thus stimulates the production of sweat in the enclosed skin area. The skin surface cannot release the sweat produced there to the environment by evaporation. Rather, the sweat, along with the noxious substances flushed out, is absorbed by a nanofiber nonwoven and retained in a superabsorbent. Alternatively, the carrier layer 10 may include a coating and/or an intermediate layer impermeable to water vapor.

In addition, at least one of the carrier layer 10 or the active layer 20 can be configured so as to be permeable to heat radiation and/or heat conducting. The skin areas concerned which are covered by the textile composite material 12 can then be purposefully heated using heat radiators, for example, or a chemical reaction producing heat. A quick and controlled stimulation of the production of sweat in the contaminated skin area is thereby obtained. The heat transfer between the carrier layer 10 and the skin surface may take place by heat conduction. It is preferable that both the carrier layer 10 and the active layer 20 are permeable to heat radiation.

Further, at least one of the carrier layer 10 or the active layer 20 of the textile composite material 12 can be configured to be heat conducting. It is, for example, possible to insert metallic fibers or metallic filaments into the carrier layer 10 and/or the active layer 20, or provide the active layer 20 with a metallic coating. As in the embodiment described above, the skin areas concerned can be purposefully heated using appropriate heating sources such as, e.g., an electrical heating element, and the production of sweat can therefore be stimulated. The active layer 20 may also comprise a color indicator to indicate the production of sweat. Owing to this addition, the optimum time to remove the material from the skin can be indicated to the user of the textile composite material 12. Color indicators appropriate for this use are for example: Cobalt (II) chloride, quinizarin powder, pentamethoxy red, methyl yellow, phenolphthalein, thymolphthalein, p-naphtolbenzein, 4-nitrophenol, 3-nitrophenol, ocresolphthalein, m-cresol red, thymol blue, m-cresol purple, or mixtures thereof, the colors of which change if the nanofiber nonwoven has absorbed an amount of sweat that is sufficient for decontaminating and/or the capacity of the superabsorbent to absorb liquid has been exhausted. The color indicator may be combined with the superabsorbent and incorporated into the active layer 20, for example by adding the combined superabsorbent and color indicator to the polymer melt or solution before spinning of the nanofiber nonwoven.

The embodiments described above can be combined with each other in any way. The carrier layer 10 can be at the same time impermeable to water vapor and heat conducting or permeable to heat radiation, and/or the active layer 20 can contain an agent promoting the production of sweat. Further combinations are also conceivable and considered to be within the scope of the invention.

The carrier layer 10 and the active layer 20 can be formed integrally with each other. For example, the carrier layer 10 can be a woven fabric, and the nanofibers of the active layer 20 can be firmly spun onto and with the woven fabric filaments of the carrier layer 10. Preferably, the carrier layer 10 and the active layer 20 are bonded to each other. The layers can then be produced separately, so as to have the respective desired properties, and then bonded to each other by chemical, thermal or physical bonding as is generally known in the art.

Further, in a preferred embodiment, the carrier layer 10 is elastic, allowing for optimum adaptation of the textile composite material 12 to the skin. If the carrier layer 10 is elastic, then the textile composite material 12 can be adapted to the shape of the skin surface by contraction and/or expansion.

In another embodiment, the carrier layer 10 is configured to not be expandable. During the absorption of noxious substances flushed out by the sweat, the superabsorbent contained in the active layer 20 swells as a result of which the volume of the active layer 20 increases. Since the carrier layer 10 which is arranged on the side of the active layer 20 that faces away from the skin, cannot expand, this increase in volume results in that the contact between the active layer 20 and the skin surface is intensified and the active layer 20 rests more firmly on the skin area concerned, and thus further increases the effectiveness of the decontamination.

Additionally, the active layer 20 of the absorbent textile composite material 12 comprises a nanofiber nonwoven finished with a superabsorbent. The superabsorbent preferably comprises completely or mainly of polymer particles which have a skin-core structure, that is a core swelling in the presence of water and a superficially post-cured shell, and thus has a low "gel blocking" effect. The polymer particles are preferably a screening fraction of such polymer particles that have not been crushed after the superficial post-cure of the shell, prior to incorporation in the active layer 20. The polymer particles preferably have a particle size distribution of d50=55-100 µm and d100=100-150 µm and comprise (meth)acrylate or (meth)acrylate copolymer, in particular sodium polyacrylate. That is, preferably 50% of the particles have a particle size of maximum 55-100 µm, and 100% of the particles have a particle size of maximum 100-150 µm. Further, the superabsorbent may be selected from starch graft polymers such as Waterlock™, biodegradable superabsorbents, activated carbon, clay, aluminum oxide, ionic exchange resins or polyacrylates. The nanofiber nonwoven of the active layer 20 finished with the superabsorbent is made of superfine fibers or superfine filaments having a diameter of less than 10 µm, preferably of less than 1 µm, more preferably of between about 300 nm and about 900 nm and is most preferably comprised of electrostatically spun nanofibers. The nanofiber nonwoven preferably comprises fibers or filaments formed from a thermoplastic, hydrophilic or hydrophilized polymer. Most preferably, the nanofiber nonwoven is formed from polyurethane.

The nanofiber nonwovens can be produced through melt spinning, electrospinning, or gas jet spinning (NGJ) of suitable polymers. It is also contemplated that part of the nanofibers in the nonwoven can be replaced by microfibers. Materials for producing the nanofiber nonwovens comprise thermoplastic polymers selected from the group comprising polyurethane, polyamides, polyesters, polyacrylonitrile, polyvinyl alcohol, poly vinylpyrrolidone, poly ethyleneoxide, cellulose acetate, poly(ethylenimine), poly(caprolactone) and poly(2-hydroxymethacrylate), as well as mixtures thereof. Polyurethane is particularly preferred.

In order to form the active layer 20, the superabsorbent may be dusted onto a sheet of the electrostatically spun nanofiber nonwoven and mechanically integrated into the nanofiber structure. Most preferably, the superabsorbent is homogeneously dispersed in a polymer solution which is then subjected to electrostatically spinning into a nanofiber nonwoven including the superabsorbent embedded in the fiber structure.

The nanofiber nonwoven contained in the active layer 20 and finished with a superabsorbent is particularly absorbent due to the high capillarity in the nonwoven, and absorbs the noxious substances, that have to be removed, according to the existing concentration gradient between the skin surface and the nonwoven material. The noxious substances can then be effectively stored and retained by the superabsorbent. After an appropriate decontamination time of preferably about 30 seconds to 30 minutes, more preferably about 1 to 5 minutes, depending on the nature of the noxious substance, the textile composite material 12 including the absorbed noxious substances can be removed again from the skin.

Since this type of decontamination of the skin is solely based on the absorbing effect of the nanofiber nonwoven finished with a superabsorbent, a rubbing of the noxious substances into the hair follicles and the skin furrows is avoided, and the noxious substance particles are thus prevented from further entering the hair follicles or the upper cell layer of the corneocytes. The risk of a long-term effect of the noxious substances in the skin is therefore reliably excluded.

Furthermore, the adhesive layer 30 is provided on the surface of the composite material 12 that faces the skin to connect the composite material 12 with the skin and preferably comprises a skin-friendly adhesive, particularly preferably an acrylate adhesive. The addition of the adhesive layer 30 leads to an even better contact of the active layer 20 with the skin which in turn leads to an improvement of the decontaminating effect.

The protective layer 40 is optional and is removed before applying the textile composite system 12 to the skin. Furthermore, the textile composite material 12 can be configured as a cloth, a compress, a dressing or a plaster, also as an article of clothing or part of clothing for application on larger surfaces.

In view of the intended use of the textile composite material for decontaminating the skin, the nanofiber nonwoven preferably has at least one or more of the following physical properties:
 a) A fiber diameter of between 0.001 µm and 10 µm, preferably between 0.1 µm and 1.5 µm, and most preferably between 300 nm and 900 nm;
 b) An average pore size of between 0.01 µm to 500 µm, preferably less than 250 µm, more preferably less than 100 µm;
 c) A porosity, that is a percentage of the total volume of the nonwoven which is free space, of between 40% and 90%, preferably between 70% and 90%;
 d) A thickness of the active layer of between 0.1 mm to 2 mm;
 e) A density of between 0.8 to 1.5 g/cm$^3$;
 f) A mass per unit area of between 50 to 500 g/m$^2$, preferably between 50 and 400 g/m$^2$, more preferably of between 150 to 250 g/m$^2$;
 g) A breaking force and elongation (strip method), according to EDANA standard WSP 110.4 (05), of 1.5-2 MPa and 485 to 500%;
 h) An absorbency (tb) in saline (0.9% NaCl in water, 30 min), as measured in the teabag test in accordance with EDANA standard test WSP 240.2 (05), of between about 8 g/g and 10 g/g;
 i) A retention capacity (CRC) for saline (0.9% NaCl in water, 30 min), as measured in accordance with EDANA standard test WSP 241.2 (05), of between about 6 g/g to 8 g/g.

Further, the active layer composed of the nanofiber nonwoven filled with the superabsorbent preferably has at least one or more of the following properties:
 j) A filling level of superabsorbent (SAP), that is calculated as weight by weight of dry material, of between about 10 and 80%, preferably between about 40 and 80%, and most preferably between about 50 to 70%;
 k) An absorbency (tb) in saline (0.9% NaCl in water, 30 min), as measured in the teabag test in accordance with EDANA standard test WSP 240.2 (05) of between 20 g/g and 50 g/g, preferably between 25 g/g and 31 g/g, at an SAP filling level of 50%, and between about 38 g/g and 45 g/g at an SAP filling level of 75%;
 l) A retention capacity (CRC) for saline (0.9% NaCl in water, 30 min), as measured in the centrifuge test according to EDANA standard test WSP 241.2 (05), of between 14 g/g and 40 g/g, preferably between 20 g/g and 35 g/g for SAP filling levels of between 50% and 75%; and m) A contact angle as measured at 22° C. and 55% relative humidity (Fibro DAT™ of Rycobel, Belgium) of between 110° and 125°.

Figure 2:
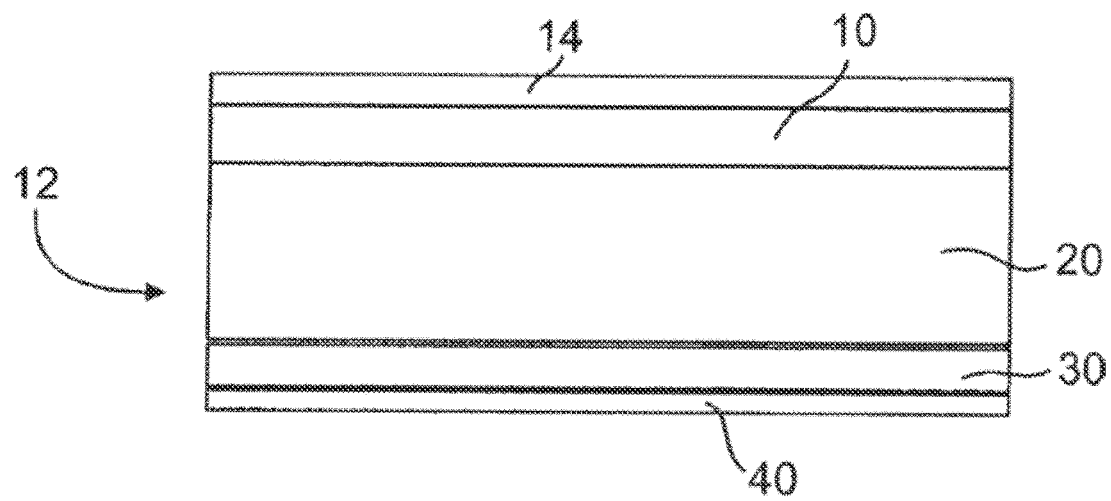
FIG. 2 illustrates a schematic cross-sectional view of another embodiment of the textile composite material in accordance with principles of the present invention.

According to the embodiment shown in FIG. 2, a barrier layer 14 impermeable to water vapor is provided in addition to the layers already illustrated in FIG. 1. The barrier layer 14 is intended to occlude the contaminated skin area and stimulate the production of sweat. In the embodiment of FIG. 2, the barrier layer 14 is formed from a material impermeable to water vapor, preferably polypropylene or PET. For an additional stimulation of the production of sweat, the barrier layer 14 and the carrier layer 10 can be configured so as to be permeable to heat radiation or to be heat conducting. An increased production of sweat by the parts of the skin covered by the barrier layer 14 or carrier layer 10 increases the decontaminating effect of the textile composite material 12. The sweat flushes out the noxious substances having already penetrated the hair follicles and the upper cell layer of the corneocytes. The sweat, along with these noxious substances and the particles of noxious substances still present on the skin surface, is then absorbed by the superabsorbent in the nanofiber nonwoven and retained therein.

At least one of the barrier layer 14 and the carrier layer 10 are configured to be permeable to heat radiation. The skin areas concerned which are covered by the textile composite material 12 can then be purposefully heated using heat radiators, for example, or a chemical reaction producing heat. A quick and controlled stimulation of the production of sweat in the contaminated skin area is thereby obtained. The heat transfer between the barrier layer 14 and the skin surface may take place by heat conduction. It is preferable that both the barrier layer 14 and the carrier layer 10 are permeable to heat radiation.

Further, the carrier layer 10 and/or the barrier layer 14 of the textile composite material 12 can be configured to be heat conducting. It is, for example, possible to insert metallic fibers or metallic filaments into the carrier layer 10 and/or the barrier layer 14, or provide the barrier layer 14 with a metallic coating. As in the embodiment described above, the skin areas concerned can be purposefully heated using appropriate heating sources such as, e.g., an electrical heating element, and the production of sweat can therefore be stimulated.

In still another embodiment, the barrier layer 14 may contain an agent promoting the production of sweat, for example by applying a sweat promoting agent onto the surface of the barrier layer 14 that faces the skin. The textile composite material 12 then acts like a transdermal system, the agent being absorbed by the skin first and stimulating the production of sweat. In contrast to transdermal systems, the sweat promoting agent does not require a long-term effect since the production of sweat is to be locally restricted and is intended to occur only for the duration of the decontamination. The sweat produced in the contaminated skin area, along with the noxious substances, is flushed out and the excessive agent is then absorbed by the nanofiber nonwoven and retained in the superabsorbent.

Suitable sweat producing agents may be methyl nicotinate, 2-hydroxyethyl salicylate, methyl salicylate, ethyl salicylate, menthol B.P. or agents containing benzene derivatives disclosed for example in JP-A 10114649.

The active layer 20 may also comprise a color indicator to indicate the production of sweat. Owing to this addition, the optimum time to remove the material from the skin can be indicated to the user of the textile composite material 12. Color indicators appropriate for this use are for example: Cobalt (II) chloride, quinizarin powder, pentamethoxy red, methyl yellow, phenolphthalein, thymolphthalein, p-naphtolbenzein, 4-nitrophenol, 3-nitrophenol, ocresolphthalein, m-cresol red, thymol blue, m-cresol purple, or mixtures thereof, the colors of which change if the nanofiber nonwoven has absorbed an amount of sweat that is sufficient for decontaminating and/or the capacity of the superabsorbent to absorb liquid has been exhausted. The color indicator may be combined with the superabsorbent and incorporated into the active layer 20, for example by adding the combined superabsorbent and color indicator to the polymer melt or solution before spinning of the nanofiber nonwoven.

The embodiments described above can be combined with each other in any way. The carrier layer 10 can be at the same time impermeable to water vapor and heat conducting or permeable to heat radiation, and/or the barrier layer 14 can contain an agent promoting the production of sweat. Further combinations are also conceivable and considered to be within the scope of the invention.

Figure 3:
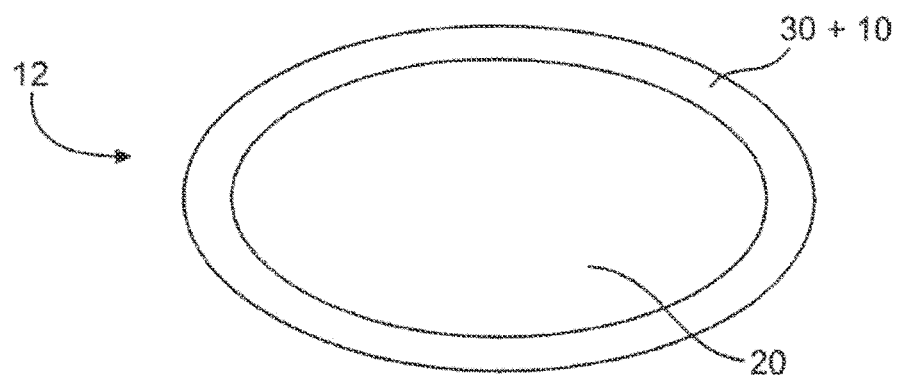
FIG. 3 illustrates a schematic view of the bottom surface of a further embodiment of the textile composite material in accordance with principles of the present invention.

Referring to the embodiment shown in FIG. 3, the textile composite material 12 has a carrier layer 10 having a planar surface area which is larger than a planar surface area of the active layer 20 so that the carrier layer 10 overlaps and encircles the rim of the active layer 20. The overlapping edge of the carrier layer 10 is provided with an adhesive layer 30. The adhesive layer 30 is provided on the surface of the composite material 12 that faces the skin to fasten the textile composite material 12 to the skin. This leads to an even better contact of the active layer 20 with the skin which in turn leads to an improvement of the decontaminating effect.

Furthermore, the adhesive layer 30 applied to the active layer 20 can be designed to remove the upper cell layer of the corneocytes from the skin. When removing the textile composite system 12 from the skin area to be decontaminated, the upper cell layer of the corneocytes, along with the noxious substance particles having already entered the latter, is thus extracted in a non-invasive way, and the proportion of the removed noxious substances is increased. In the embodiment shown, the shape of the textile composite material is chosen randomly and can of course be configured in any way.

Figure 4:
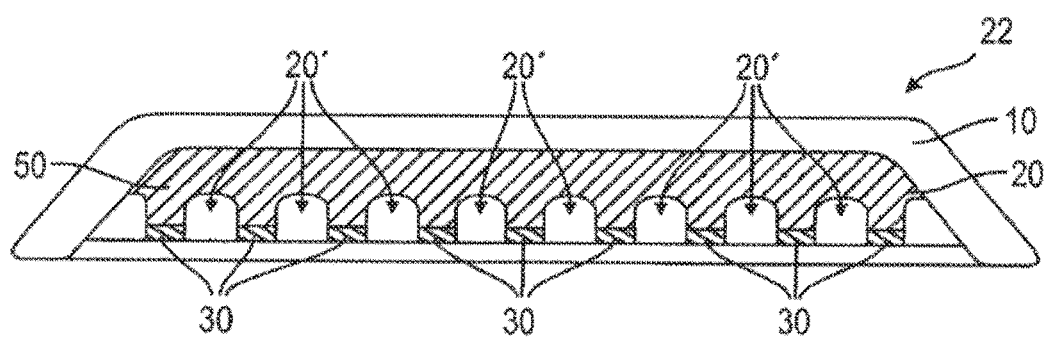
FIG. 4 illustrates a schematic cross sectional view of a further embodiment of the textile composite material in accordance with principles of the present invention.
Figure 5:
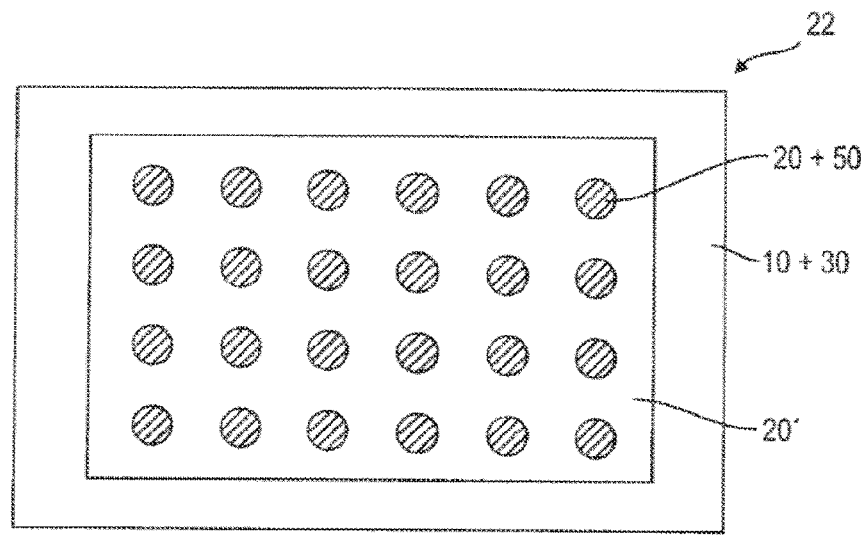
FIG. 5 illustrates a bottom view of the embodiment of FIG. 4 in accordance with principles of the present invention.

A further embodiment is shown with reference to FIGS. 4 and 5. In this embodiment, the composite textile material 22 comprises the flexible carrier layer 10, and a first and second active layer 20, 20', wherein the first active layer 20 is provided with a metal coating 50. The nanofiber nonwoven constituting the first active layer 20 is produced to form peaks and valleys. The valleys of the first active layer 20 are filled with the second active layer 20'. At least the second active layer 20' is comprised of the nanofiber nonwoven filled with superabsorbent. Preferably, both of the first and second active layer 20, 20' include the superabsorbent. The adhesive layer 30 is provided on the metallic coating 50 (as shown in FIG. 4), or on the edge portion of the carrier layer 10 overlapping the rim of the active layers 20, 20', (as shown in FIG. 5). The method for forming the peaks and valleys comprises manipulating the fibers during the spinning process either with a vacuum or with grids. The peaks and valleys were created to allow for both the absorptive component 20' and the heat-conducting component 50 to be in direct contact with the skin. The benefit is that the metallic coating 50, which acts as a heat-conducting component, needs to be in direct contact with the skin in order to be conductive. However, if the entire surface is coated, then the skin has no direct contact with the absorptive layer, and thus will not have optimal absorption of contaminate. By creating the peaks and valleys, you have both the absorptive layer 20' in direct contact, as well as the conductive layer 50.

The following is a description of the tests performed on volunteers to show the capability of the inventive textile composite material to effectively decontaminate the human skin.

Test Materials and Methods

A) Textile Composite:

The absorbent textile composite used in these tests comprises an active layer comprised of a thermoplastic polyurethane-based nanofiber nonwoven filled with LUQUASORB™ (BASF SE, Ludwigshafen, Germany) having a skin-core structure and a particle size distribution of d50=55-100 μm and d100=100-150 μm. Other parameters of the nonwoven and composite were as follows:

- a fiber diameter of between 300 nm and 1 μm;
- an pore size of between 0.01 μm to 500 μm;
- a porosity that is a percentage of the total volume of the nonwovens, which is free space, of about 80%;
- a thickness of the active layer of about 0.5 mm;
- a mass per unit area of about 230 g/m$^2$;

Further, the active layer comprised of the nanofiber nonwoven filled with the superabsorbent preferably had the following properties:

- a filling level of superabsorbent that is calculated as weight by weight of dry material, of about 50%;
- an absorbency (tb) measured in the teabag test in accordance with EDANA standard test WSP 240.2 (05) of about 28 g/g (saline, 0.9% NaC in water, 30 min);
- a retention capacity (CRC) measured in the centrifuge test according to EDANA standard test WSP 241.2 (05), of about 24 g/g; and
- a contact angle as measured at 22° C. and 55% relative humidity (Fibro DAT™ of Rycobel, Belgium) of about 121°.

B) Model Formulation and Skin Treatment:

A waterproofed sunscreen containing 3% of the UV-filter substance octylmethoxycinnamate was applied onto the skin on the flexor forearm of 10 healthy volunteers. The sunscreen was chosen as a model formulation because it sticks strongly on the skin surface after application. 2 mg/cm$^2$ of the sunscreen was applied on selected skin areas at a size of 4×5 cm$^2$ for each area. The application areas were surrounded with a silicon barrier to avoid the spreading of the formulation on the skin surface. After 10 minutes penetration time, the penetration of the formulation into the skin was analyzed by the method of tape stripping as described below.

C) Decontamination:

The decontamination was performed on one skin area by washing for 30 seconds under running water with soap.

A second skin area was used as a control without decontamination.

All other skin areas were decontaminated with the absorbent textile composite which was pressed onto the skin for 1 minute, without applying a washing or massage procedure, and finally removed.

D) Tape Stripping:

The tape stripping test is based on the successive application and removal of adhesive films (Tesa Film, Beiersdorf, Hamburg) from the skin. The removed tape strips comprise approximately one cell layer of corneocytes and the corresponding part of topically applied substance localized within this cell layer. The amount of stratum corneum removed with a single tape strip is determined spectroscopically by determining the pseudo-absorption at 430 nm, whilst the concentration of the penetrated formulation is analyzed by the absorption of the UV-filter substance octylmethoxycinnamate at 310 nm.

Figure 6:
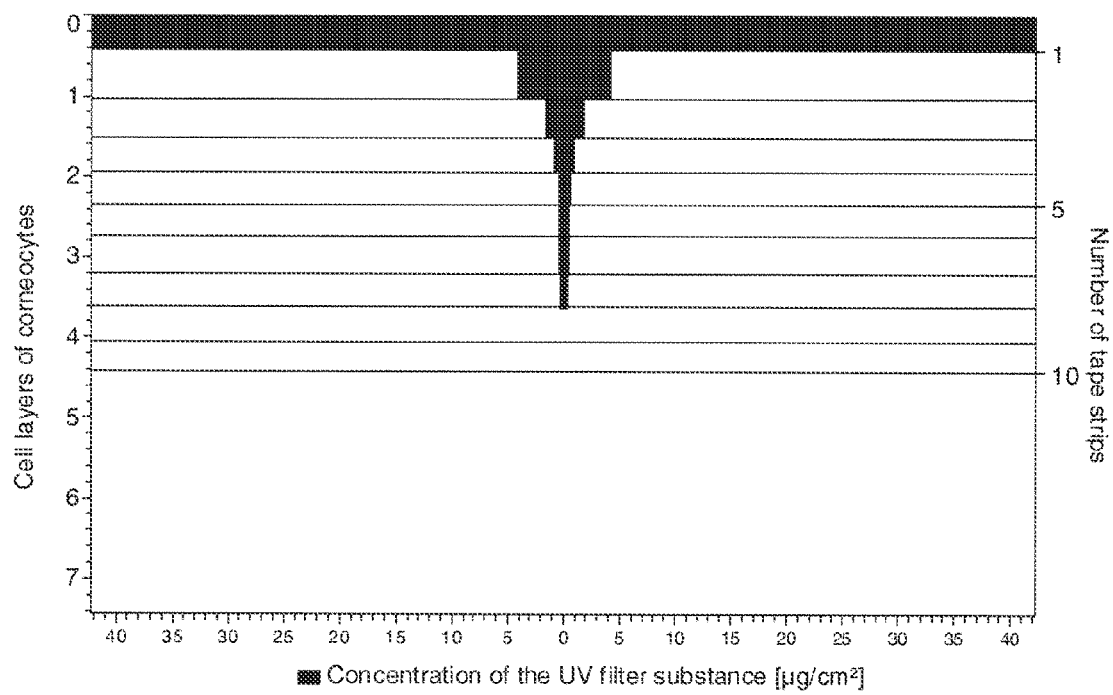
FIG. 6 is a graph illustrating the penetration profile of a model substance into the skin obtained by tape stripping in accordance with principles of the present invention.

Ten tape strips were removed from each skin area. The horny layer profile of the skin areas was calculated as described by Weigmann et. al., "Determination of the horny layer profile by tape stripping in combination with optical spectroscopy in the visible range as a prerequisite to quantify percutaneous absorption" in Skin Pharmacol. Appl. Skin Physiol. (1999), vol. 12, pp. 34-45, which is incorporated by reference. Specifically, the horny layer profile of the skin areas was calculated by adding the pseudo-absorptions of the single tape strips removed from the same skin area. The penetration profile was determined by relating the amount of the penetrated UV filter substance to the corresponding tape strip in the horny layer profile. A typical example is shown in FIG. 6, wherein the distance between the horizontal lines corresponds to the amount of stratum corneum removed with a single tape strip. The upper horizontal lines represent the skin surface and the lower horizontal lines correspond to deeper parts of the stratum corneum.

The concentration of the UV filter octylmethoxycinnamate in the different samples was determined by absorption, using an UV/VIS spectrometer. The UVNIS spectra of the extracts were measured between 240 and 500 nm. The concentration of the UV filter substance was calculated from the determined absorption maximum at 310 nm on the basis of a calibration curve in ethanol.

E) In Vivo Laser Scanning Microscopy (LSM):

The commercially available in vivo laser scanning microscope (Stratum™, Optilas, Melbourne, Australia) was used for the detection of the fluorescent model substance on the skin surface and in the upper layers of the skin. The excitation wavelength of the Argon laser used was 480 nm. The basic station of the LSM was connected to a handpiece with optical fibers. Optical imaging and focus systems were located within the handpiece Skin areas under investigation were sized at 250×250 μm$^2$.

The fluorescence intensity and the distribution of the model substance was determined on all skin areas immediately before and after the decontamination.

Results

Figure 7:
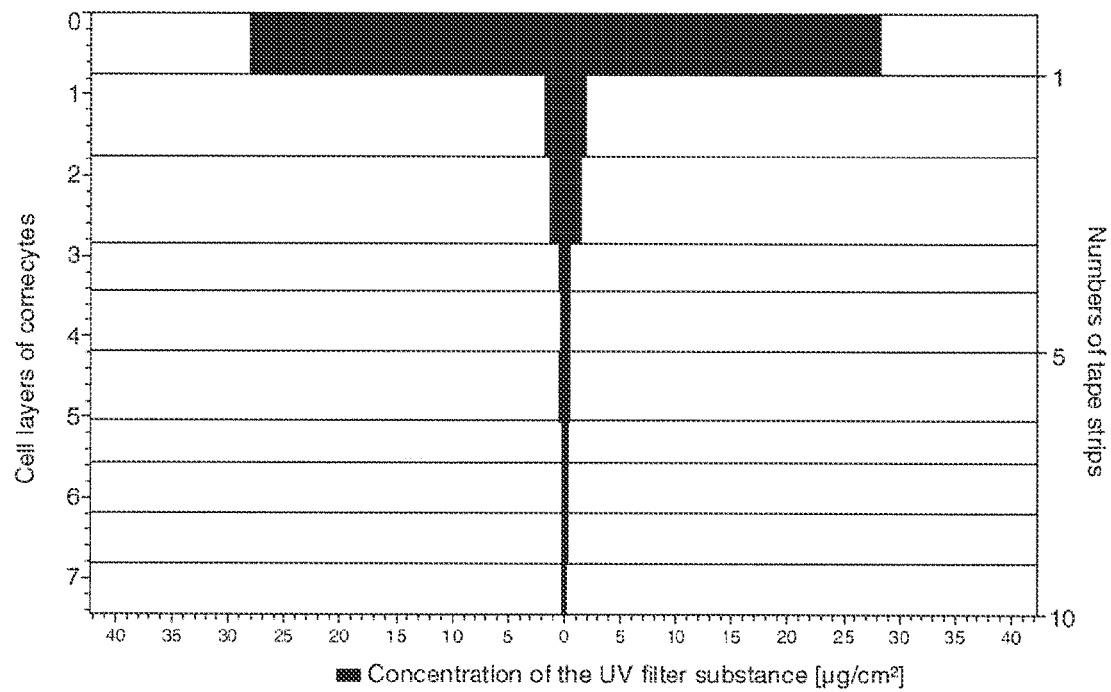
FIG. 7 is a graph illustrating the distribution of the model substance in the stratum corneum after washing in accordance with principles of the present invention.

FIG. 6 is a graph illustrating the penetration profile of a model substance into the skin obtained by tape stripping. Specifically, FIG. 6 shows the typical penetration profile of the UV filter octylmethoxycinnamate, 10 minutes after application without decontamination obtained from skin area A. Most of the formulation is located in the first cell layers. The UV filter substances could be detected up to the 7$^{th}$ cell layers of corneocytes. About 90% of the topically applied UV filter can be detected in the first 10 tape strips, FIG. 7 is a graph illustrating the distribution of the model substance in the stratum corneum after washing. Specifically, in FIG. 7, the distribution of the UV filter substance in the stratum corneum after washing is demonstrated. The results depicted in FIG. 7 show that the amount of UV filter substance in the upper cell layer was reduced by the washing procedure to about 60%. However, the UV filter substance could be detected in deeper layers in comparison to the penetration profile shown in FIG. 6.

Figure 8:
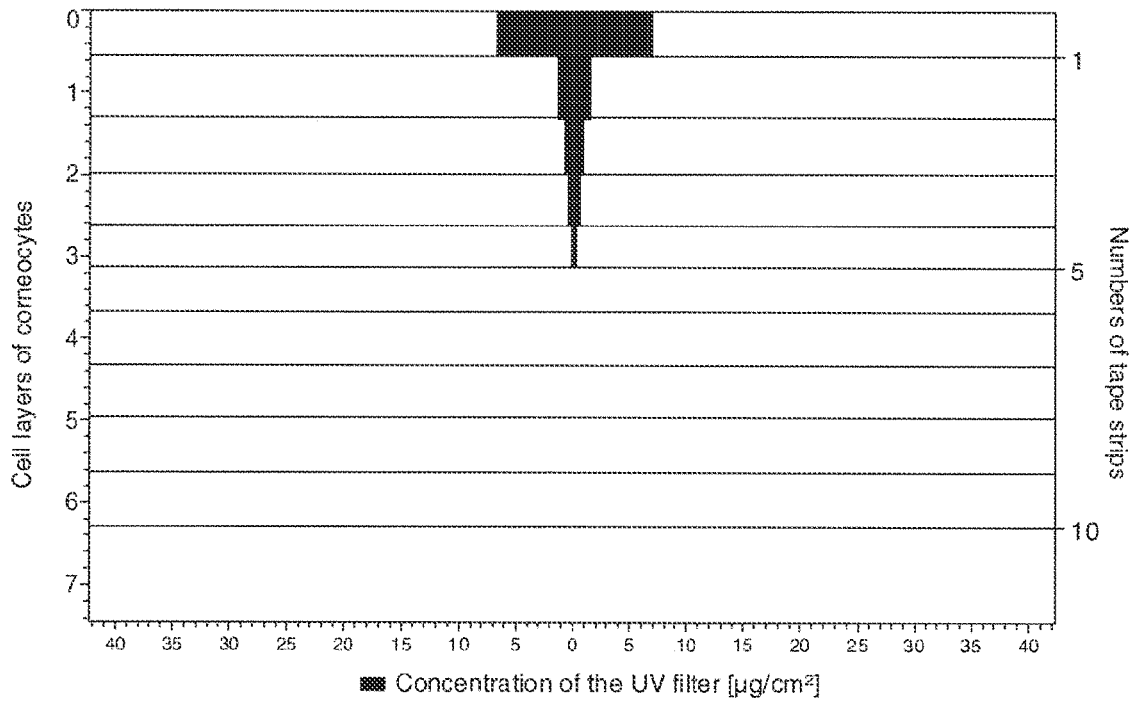
FIG. 8 is a graph illustrating the distribution of the model substance in the stratum corneum after decontamination with a textile composite material composed of nanofiber nonwoven filled with superabsorbent in accordance with principles of the present invention.

FIG. 8 is a graph illustrating the distribution of the model substance in the stratum corneum after decontamination with a textile composite material composed of nanofiber nonwoven filled with superabsorbent. Specifically, in FIG. 8, the penetration profiles after decontamination with the absorbent textile composite material are presented. In this case, the concentration of the octylmethoxycinnamate was reduced strongly in the stratum corneum in comparison to the washed skin area B. Specifically, a reduction to about 35% of the initial UV filter concentration was found in the case of skin decontamination with the textile composite material. A penetration in deeper parts of the stratum corneum as in the case of washing was not observed.

Similar results were obtained for use of an absorbent textile composite comprising an active layer comprised of the nanofiber nonwoven and the superabsorbent, and an absorbent textile composite material having a sandwich structure, respectively, wherein the active layer comprises a top and bottom cover layer formed from a nanofiber nonwoven without a superabsorbent, and a base layer comprised of the nanofiber nonwoven filled with superabsorbent and arranged between said top and bottom cover layer.

Therefore, use of the textile composite material for decontaminating the skin resulted in a removal of about 70% of the model formulation from the skin. In the case of decontamination with the textile composite, no massage was applied, so that the decontamination procedure does not stimulate the penetration into the hair follicles. Usually, hair follicles act as a long term reservoir for topically applied substances providing significantly increased storage times in comparison to the stratum corneum. Additionally, the hair follicles contain or are surrounded by several important target structures, such as blood capillaries, stem and dendritic cells. Here, hazardous substances can exhibit strong destructive activities. The advantage of decontamination with the absorbent textile composite materials is that it can be carried out immediately without the utilization of water, which is not always available at the required time. Efficient methods for skin decontamination may be not only important in the case of industrial or research accidents, but also in relation to terrorist attacks.

Figure 9:
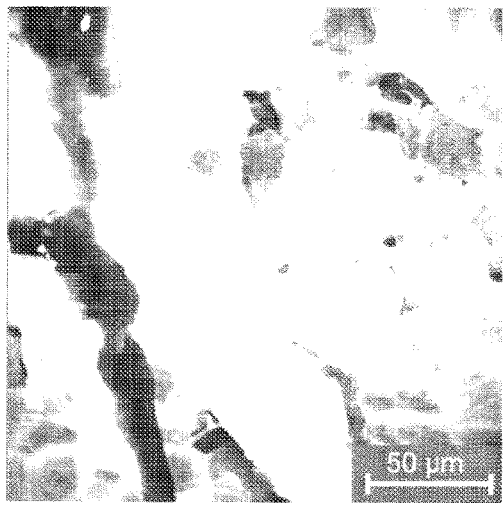
FIG. 9 illustrates a laser scanning microscope (LSM) image of the distribution of a fluorescent dye on the skin after application and penetration in accordance with principles of the present invention.

Typical images of the distribution of the fluorescent model substance on the skin surface by LSM measurements, with and without decontamination, are presented in FIGS. 9 to 11. Specifically, FIG. 9 illustrates an LSM image of the distribution of a fluorescent dye on the skin after application and penetration. Without decontamination, a strong fluorescent signal was detected on the skin surface (FIG. 9).

Figure 10A:
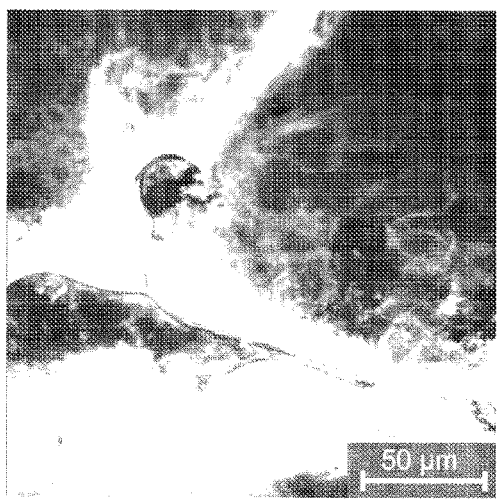
FIGS. 10a-b illustrate an LSM image of the distribution of the fluorescent dye after washing in accordance with principles of the present invention.
Figure 10B:
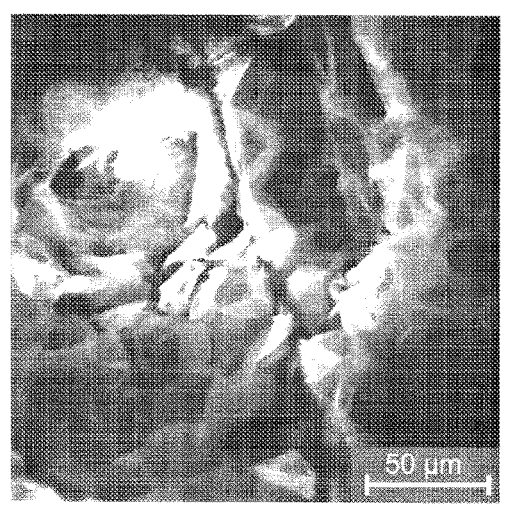

FIGS. 10*a-b* illustrate an LSM image of the distribution of the fluorescent dye after washing. The washing procedure led to a removal of the topically applied substance from the skin surface. However, a strong fluorescent signal was still localized in the region of the furrows and orifices of the hair follicles (FIGS. 10*a, b*).

Figure 11A:
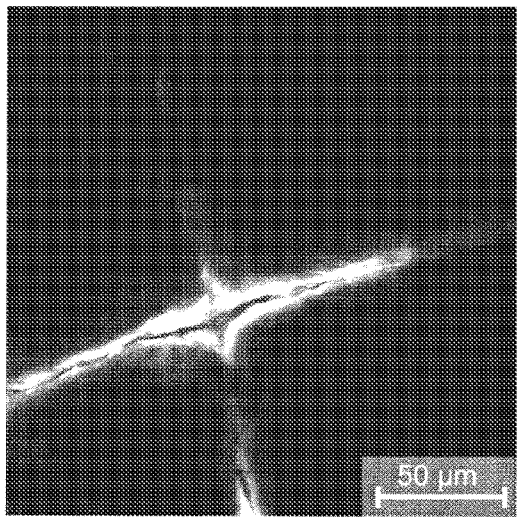
FIGS. 11a-c illustrate an LSM image of the distribution of the fluorescent dye after decontamination with the textile composite material in accordance with principles of the present invention.
Figure 11B:
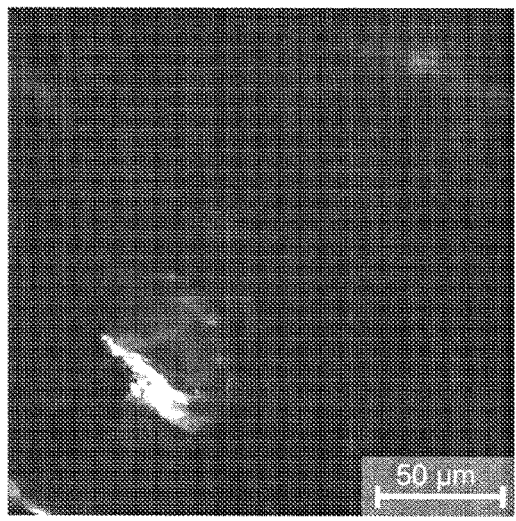
Figure 11C:
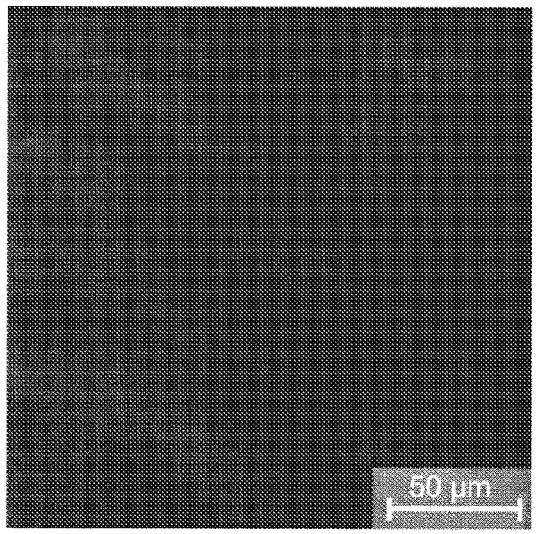

FIGS. 11*a-c* illustrate an LSM image of the distribution of the fluorescent dye after decontamination with the textile composite material. After decontamination with the absorbent material, the fluorescent signal was markedly reduced, both on the skin surface as well as in the furrows and orifices of the hair follicles. However, in FIGS. 11*a-b*, a low fluorescent signal was still detectable in the area of the furrows and orifices of the hair follicles (FIG. 11 *a, b*).

Furthermore, it was found that extending the application time of the absorbent textile composite beyond 1 minute did not improve the decontamination effect. However, as shown in FIG. 11*c*, a repeated application of the absorbent material on the same skin area led to an almost complete removal of the fluorescent model substance from the furrows and orifices of the hair follicles (FIG. 11*c*).

Figure 12:
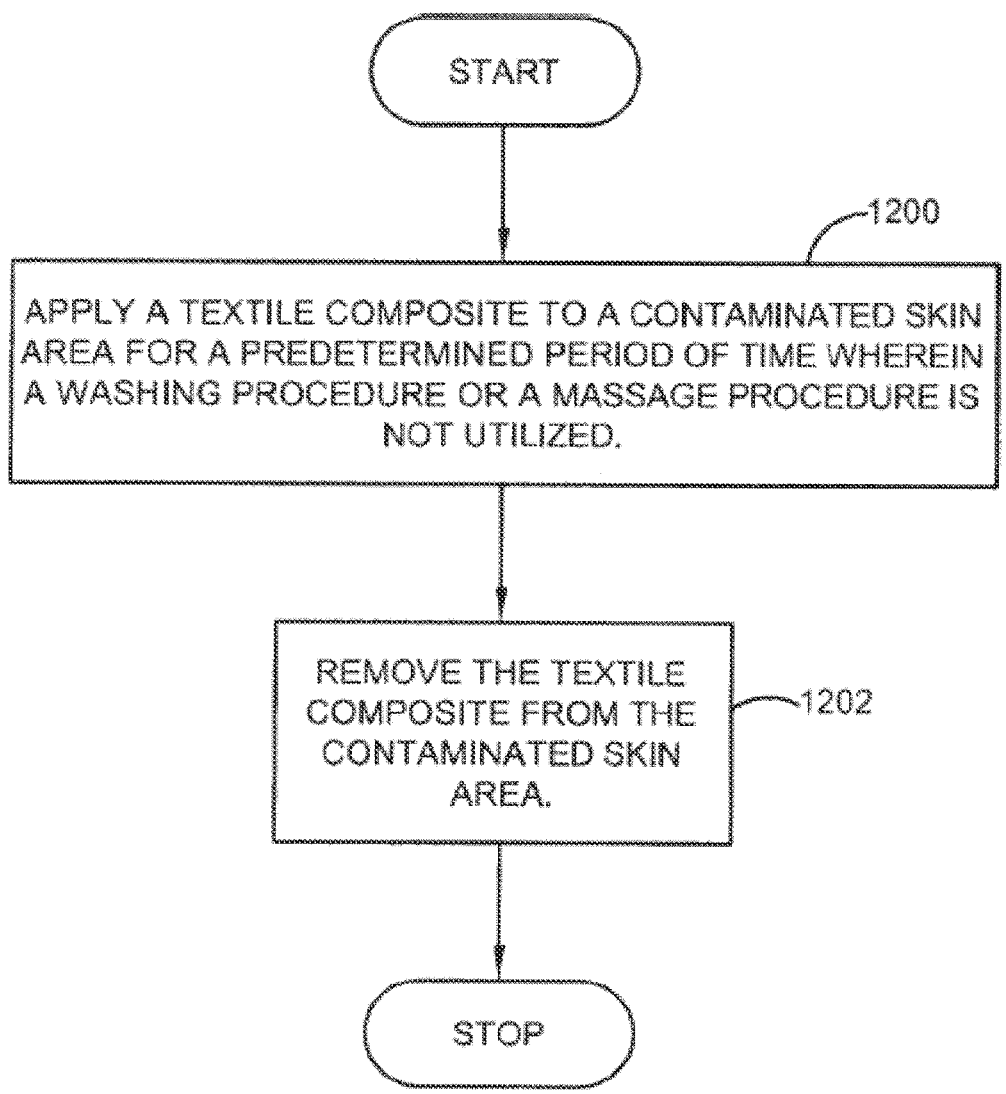
FIG. 12 is a flow chart illustrating the method of decontaminating human skin from noxious substances in accordance with principles of the present invention.
Figure 13:
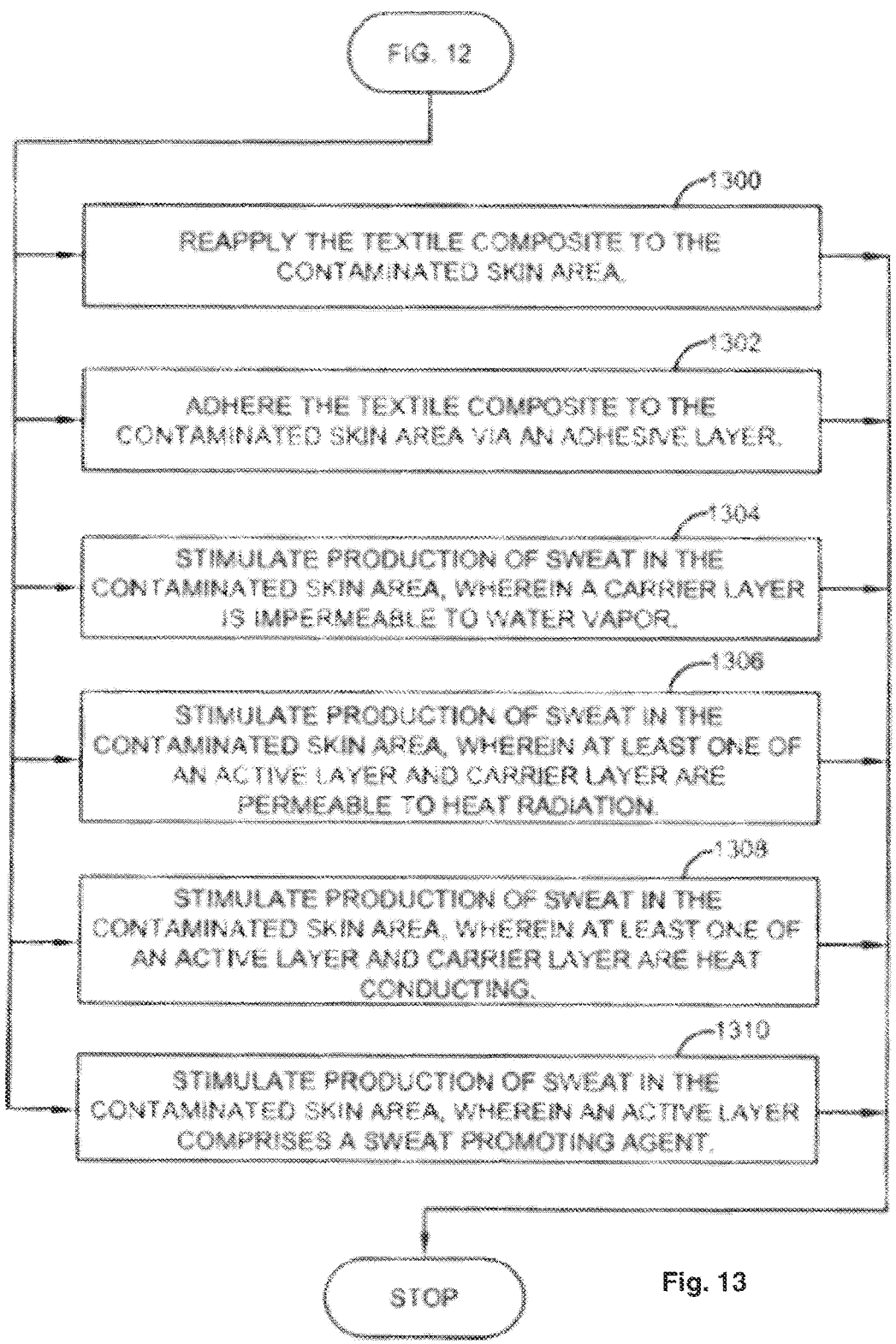
FIG. 13 is a flow chart illustrating further steps in the method of decontaminating human skin from noxious substances in accordance with principles of the present invention.

FIGS. 12-13 illustrate methodologies of decontaminating human skin from noxious substances, according to various aspects of the innovation. While, for purposes of simplicity of explanation, the one or more methodologies shown herein (e.g., in the form of a flow chart or flow diagram) are shown and described as a series of acts, it is to be understood and appreciated that the subject innovation is not limited by the order of acts, as some acts may, in accordance therewith, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the innovation.

Referring to FIG. 12, a method of decontaminating human skin from noxious substances is illustrated. At 1200, a textile composite is applied to a contaminated skin area for a predetermined period of time. The textile composite is applied to the contaminated skin area without applying a washing procedure or a massage procedure. Furthermore, the textile composite comprises an active layer comprising a nanofiber nonwoven which comprises a superabsorbent for absorbing and retaining at least one noxious substance. And, at 1202 the textile composite is removed from the contaminated skin area.

Referring to FIG. 13, the method of decontaminating human skin from noxious substances is further illustrated. At 1300, the textile composite is reapplied to the contaminated skin area. As stated supra, it was found that extending the application time of the textile composite beyond the predetermined time period did not improve the decontamination effect. However, a repeated application of the textile composite on the same contaminated skin area led to an almost complete removal of the noxious substance from the contaminated area as well as the furrows and orifices of the hair follicles.

And at 1302, the textile composite is adhered to the contaminated skin area via an adhesive layer. The adhesive layer is applied to the active layer and connects the composite material with the contaminated skin area. Furthermore, the adhesive layer can be designed to remove the upper cell layer of the corneocytes from the skin. When removing the textile composite from the contaminated skin area, the upper cell layer of the corneocytes, along with the noxious substance particles is extracted in a non-invasive way, and the proportion of the removed noxious substances is increased.

At 1304, the production of sweat is stimulated in the contaminated skin area, wherein a carrier layer is impermeable to water vapor. An increased production of sweat by the parts of the skin covered by the active layer or carrier layer increases the decontaminating effect of the textile composite. The sweat flushes out the noxious substances having already penetrated the hair follicles and the upper cell layer of the corneocytes. The sweat, along with these noxious substances and the particles of noxious substances still present on the skin surface, is then absorbed by the superabsorbent in the nanofiber nonwoven and retained therein. In a specific embodiment, the textile composite material has a carrier layer that is impermeable to water vapor. The carrier layer which is impermeable to water vapor closes the active layer lying on the contaminated skin surface in a damp-tight manner and thus stimulates the production of sweat in the enclosed skin area.

At 1306, the production of sweat is stimulated in the contaminated area, wherein at least one of the active layer and the carrier layer are configured to be permeable to heat radiation. At least one of the carrier layer and the active layer are designed to stimulate the production of sweat by the skin. The skin areas concerned which are covered by the textile composite can then be purposefully heated using heat radiators, for example, or a chemical reaction producing heat. A quick and controlled stimulation of the production of sweat in the contaminated skin area is thereby obtained.

At 1308, the production of sweat is stimulated in the contaminated area, wherein at least one of an active layer and a carrier layer of the textile composite material are configured to be heat conducting. It is, for example, possible to insert metallic fibers or metallic filaments into the carrier layer and/or the active layer, or provide the active layer with a metallic coating. As in the embodiment described above, the skin areas concerned can be purposefully heated using appropriate heating sources such as, e.g., an electrical heating element, and the production of sweat can therefore be stimulated.

At 1310, the production of sweat is stimulated in the contaminated area, wherein an active layer comprises an agent promoting the production of sweat. For example, by applying a sweat promoting agent onto the surface of the active layer that faces the skin, the agent will stimulate the production of sweat to flush out the noxious substances. The textile composite material then acts like a transdermal system, the agent being absorbed by the skin first and stimulating the production of sweat.

Suitable sweat producing agents may be methyl nicotinate, 2-hydroxyethyl salicylate, methyl salicylate, ethyl salicylate, menthol B.P. or agents containing benzene derivatives disclosed for example in JP-A 10114649.

Furthermore, the active layer may also comprise a color indicator to indicate the production of sweat. Owing to this addition, the optimum time to remove the material from the skin can be indicated to the user of the textile composite material. Color indicators appropriate for this use are for example: Cobalt (II) chloride, quinizarin powder, pentamethoxy red, methyl yellow, phenolphthalein, thymolphthalein, p-naphtolbenzein, 4-nitrophenol, 3-nitrophenol, ocresolphthalein, m-cresol red, thymol blue, m-cresol purple, or mixtures thereof, the colors of which change if the nanofiber nonwoven has absorbed an amount of sweat that is sufficient for decontaminating and/or the capacity of the superabsorbent to absorb liquid has been exhausted. The color indicator may be combined with the superabsorbent and incorporated into the active layer, for example by adding the combined superabsorbent and color indicator to the polymer melt or solution before spinning of the nanofiber nonwoven.

The embodiments described above can be combined with each other in any way. The carrier layer can be at the same time impermeable to water vapor and heat conducting or permeable to heat radiation, and/or the active layer can contain an agent promoting the production of sweat. Further combinations are also conceivable and considered to be within the scope of the invention.

The carrier layer and the active layer can be formed integrally with each other. For example, the carrier layer can be a woven fabric, and the nanofibers of the active layer can be firmly spun onto and with the woven fabric filaments of the carrier layer. Preferably, the carrier layer and the active layer are bonded to each other. The layers can then be produced separately, so as to have the respective desired properties, and then bonded to each other by chemical, thermal or physical bonding as is generally known in the art.

Additionally, it is also contemplated that the above layers can be interchangeable without affecting the overall concept of the invention. Illustrative aspects are described herein in connection with the following description and the annexed drawings to further illustrate such interchangeability. These aspects are indicative, however, of but a few of the various ways in which the layers disclosed herein can be employed and interchanged, and the contemplated invention is intended to include all such aspects and their equivalents.

Further, what has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method of decontaminating human skin from noxious substances, comprising:
    applying a textile composite to a contaminated skin area for a predetermined period of time;
    stimulating production of sweat in the contaminated skin area; and
    removing the textile composite from the contaminated skin area;
    wherein the textile composite comprises a nanofiber nonwoven and a superabsorbent integrated into the nanofiber nonwoven, the nanofiber nonwoven having a fiber diameter of less than 1 μm; and
    wherein the contaminated skin area comprises contaminated hair follicles, and the noxious substances are removed from the hair follicles.

2. The method of decontaminating human skin from noxious substances of claim 1, further comprising:
    reapplying the textile composite to the contaminated skin area; and
    adhering the textile composite to the contaminated skin area via an adhesive layer.

3. The method of decontaminating human skin from noxious substances of claim 1, wherein a carrier layer is impermeable to water vapor.

4. The method of decontaminating human skin from noxious substances of claim 1, wherein the nanofiber nonwoven and the superabsorbent integrated into the nanofiber nonwoven form an active layer, wherein at least one of the active layer and a carrier layer are permeable to heat radiation.

5. The method of decontaminating human skin from noxious substances of claim 1, wherein the nanofiber nonwoven and the superabsorbent integrated into the nanofiber nonwoven form an active layer, wherein at least one of the active layer and a carrier layer are heat conducting.

6. The method of decontaminating human skin from noxious substances of claim 1, wherein the nanofiber nonwoven and the superabsorbent integrated into the nanofiber nonwoven form an active layer, wherein the active layer further comprises a sweat promoting agent.

\* \* \* \* \*